United States Patent [19]

Tobkes et al.

[11] 4,196,200

[45] Apr. 1, 1980

[54] ANTIBIOTIC BM123-DIOCTYL SULFOSUCCINATE COMPLEXES

[75] Inventors: Martin Tobkes, Spring Valley; Murray Dann, Pearl River, both of N.Y.

[73] Assignee: American Cyanamid Company, Stamford, Conn.

[21] Appl. No.: 874,308

[22] Filed: Feb. 2, 1978

[51] Int. Cl.$^2$ ...................... A61K 31/70; A61K 31/71
[52] U.S. Cl. .................................... 424/180; 424/181; 536/17 R
[58] Field of Search ................... 536/17; 424/181, 180

[56] References Cited

U.S. PATENT DOCUMENTS 4,007,167  2/1977  Mautin et al. ..................... 536/17

*Primary Examiner*—Jerome D. Goldberg
*Attorney, Agent, or Firm*—Edward A. Conroy, Jr.

[57] ABSTRACT

This disclosure describes reversible complexes of antibiotic trans-BM123γ with a dioctyl sulfosuccinate salt and a process for preparing same. The complexes are useful as animal feed supplements which significantly enhance the growth rate of animals and poultry.

11 Claims, No Drawings

ANTIBIOTIC BM123-DIOCTYL SULFOSUCCINATE COMPLEXES

BRIEF SUMMARY OF THE INVENTION

This invention relates to a method of recovering antibiotic trans-BM123$_\gamma$ from fermentation whole harvest mashes containing it. More particularly, the process involves adding a dioctyl sulfosuccinate salt (or mixtures thereof) either to the whole harvest mash or to the filtered fermentation liquor, and recovering the so precipitated reversible complex by any convenient means. The invention also relates to the use of the so prepared complexes in animal feed supplement compositions for enhancing the growth rate of animals such as poultry, swine, early weaned pigs, and ruminants such as cattle, sheep and goats.

Antibiotic trans-BM123$_\gamma$ is formed by fermentative biosynthesis during the cultivation under controlled conditions of new strains of an undetermined species of Nocardia NRRL 5646, NRRL 8050, NRRL 11,230 and mutants thereof. The preparation and properties of antibiotics trans-BM123$_{\gamma 1}$, trans-BM123$_{\gamma 2}$, and trans-BM123$_\gamma$ are set forth in U.S. Pat. No. 4,007,167 which is hereby incorporated by reference. Hereinafter, trans-BM123$_\gamma$ refers to a mixture in any proportions of trans-BM123$_{\gamma 1}$ and trans-BM123$_{\gamma 2}$. The problem of recovering the antibiotic economically has been a serious one. In the patent referred to above, adsorption on carbon followed by elution and column chromatography are employed. Such a process is not excessively expensive where pure antibiotic is required for medical usage. However, when the antibiotic is to be used in animal feed supplement compositions the factor of cost is a very serious matter and there is, therefore, a need for an inexpensive process of recovering the antibiotic for this purpose.

The present invention deals with a process and in a more specific aspect also with a product. The process involves the precipitation of the antibiotic either from the whole harvest mash or from the filtered fermentation broth by the addition of a dioctyl sulfosuccinate salt. The dioctyl sulfosuccinate salts operable in the novel process of the present invention are those prepared from sulfobutanedioic acid 1,4-bis(2-ethylhexyl)ester and the alkali metal or alkaline earth metal cations. Typical such salts are dioctyl sodium sulfosuccinate, dioctyl potassium sulfosuccinate, dioctyl calcium sulfosuccinate, dioctyl magnesium sulfosuccinate, etc. The preparation and properties of these dioctyl sulfosuccinate salts are set forth in U.S. Pat. Nos. 2,028,091, 2,176,423, and 3,035,973. Mixtures of dioctylsulfosuccinate salts may also be employed such as a mixture of dioctyl lithium sulfosuccinate and dioctyl barium sulfosuccinate. When mixtures of dioctyl sulfosuccinate salts are employed, then a corresponding mixture of antibiotic-complexes are obtained.

The novel process of the present invention provides almost complete removal of the antibiotic activity from the fermentation mash or broth. Furthermore, the antibiotic dioctyl sulfosuccinate complex so obtained can be used, without separation of the constituents, in animal feed supplement compositions, which is an important economic advantage. Therefore, in one of the aspects of the present invention the complexes of antibiotic trans-BM123$_\gamma$ and dioctyl sulfosuccinate salts are included as products.

The product of the antibiotic and a dioctyl sulfosuccinate salt has been referred to as a reversible complex. Its exact chemical nature has not been determined, but covalent bonding is not involved and the product is not a physical mixture. This complex, derived from the interaction of the antibiotic and a dioctyl sulfosuccinate salt, is not necessarily combined in any limiting stoichiometry. The chemical bonds are reversible, since the antibiotic trans-BM123$_\gamma$ may be recovered from the complex by various means. While it is not intended to limit the present invention to theories of chemical constitution and the like, it seems probable that the complex of the present invention is sufficiently reversible so that under conditions of use in animal feed supplement compositions the antibiotic is set free upon ingestion.

As starting material for the novel process of the present invention, there may be employed the whole harvest mash obtained after completion of a fermentation with Nocardia sp. NRRL 5646, NRRL 8050, NRRL 11230 or mutants thereof. Preferably, there is employed the fermentation liquor or broth which has been clarified by removing the mycelia and other insolubles by filtration. Diatomaceous earth or any other conventional filtration acid may be used to assist in the filtration. The pH of the whole harvest mash or the filtered broth is first adjusted to between 2.5 and 6.0 with dilute aqueous acid. Suitable acids for this purpose may be, for example, dilute hydrochloric acid, dilute sulfuric acid, dilute trifluoroacetic acid, etc., although even glacial acetic acid may be used. Then an aqueous solution of a dioctyl sulfosuccinate salt (or a mixture thereof) is added slowly, with stirring, at ambient temperature. Diatomaceous earth is added and the antibiotic and the dioctyl sulfosuccinate salt form a complex which is water insoluble and thus precipitates. The precipitated complex or, in the case of the whole mash, the precipitated complex together with the fermentation mash solid, is recovered by filtration or centrifugation and dried. The products so obtained may be dried by slurrying the wet solids in polar, water miscible liquids such as acetone (which do not act as solvents for the complex) followed by filtration, rinsing and air-drying or by re-slurrying the wet solids in water and freeze drying or spray drying. When the products of the present invention are thus carefully dried under temperature conditions which do not degrade antibiotic trans-BM123$_\gamma$, they are usually tan to brown colored solids.

The amount of dioctyl sulfosuccinate salt added to precipitate the complex with the antibiotic is normally the minimum required to form the complex with the antibiotic. The amount of dioctyl sulfosuccinate salt required is, however, directly proportional to the antibiotic concentration in the mash or liquor. The specific bioactivity of the precipitated complex also varies and it is, in fact, likely that the complex has varying relative amounts of antibiotic.

The minimum amount of dioctyl sulfosuccinate salt required to form the complex with the antibiotic in any particular fermentation batch may be readily determined as follows. A sample (conveniently 50–100 ml.) of the fermentation whole harvest mash is taken and clarified by removing the mycelia and other insolubles by filtration, preferably with a filter aid. The filtrate is then acidified to a pH of 2.5 to 4.8 with dilute aqueous mineral acid. This solution is then titrated with the particular aqueous solution of dioctyl sulfosuccinate salt which is to be used until no further precipitate or turbidity forms. The amount of dioctyl sulfosuccinate salt solution for the fermentation batch is then calculated from the titer of the sample taken.

This invention also relates to animal feed supplement compositions effective in accelerating the growth rate of animals and poultry. In recent years, the use of antibiotics in animal feeds for improving growth characteristics and efficiency of feed utilization has become of considerable economic importance. In accordance with the present invention, the dried dioctyl sulfosuccinate complex of the dried harvest mash solids containing the dioctyl sulfosuccinate complex, either alone or in combination with suitable carriers, when added to an animal feed, aid in increasing the growth rate. In addition, feed efficiency is improved. The present invention has the advantage that the growth rate of non-ruminants such as poultry and swine, and especially weanling pigs, is significantly increased, and that feed conversion rates are noticeably enhanced.

The feed supplement compositions of the present invention are administered in an amount sufficient to furnish approximately the following dosage levels in mg./head/day.

Large ruminants —350
Small ruminants —200
Non-ruminants —100
Poultry —2

The mg./lb. of antibiotic trans-BM123$\gamma$ present in any particular supplement composition of the present invention may be readily determined as follows: Products may be assayed by high pressure liquid chromatography. Material is dissolved in methanol at a level of 0.5 mg./ml. and diluted with a 0.01 M solution of sodium heptanesulfonate in 2% aqueous acetic acid to a final concentration of 0.25 mg./ml. and filtered. The filtered solution is injected into a Waters Associates $\mu$ Bondapak ® C-18 column and developed with solvent containing 0.005 M sodium heptanesulfonate and 1% acetic acid in 50% methanol, using a flow rate of one ml./minute. Eluate from the column is monitored at 286 nm at a sensitivity of 0.04 AFS. Chromatographic retention times are identical to that of an authentic sample of trans-BM123$\gamma$ hydrochloride.

Alternatively, the milligrams per pound of antibiotic trans-BM123$\gamma$ present in any particular supplement composition may be readily determined by bioassay. The preferred method is an adaptation of the *Staphylococcus aureus turbidimetric assay for tetracycline that is described in the manual "Assay Methods of Antibiotics, a Laboratory Manual" by D. C. Grove and W. A. Randall, Medical Encyclopedia Inc.* (1955) pages 48–52, substituting *Klebsiella pneumoniae* as the test organism. From the potency data thus obtained, the pounds of feed supplement composition to be used per ton of feed may be readily calculated.

A wide variety of carriers may be used in the preparation of the feed supplement compositions of this invention containing the dried dioctyl sulfosuccinate complex or the dried harvest mash solids containing the dioctyl sulfosuccinate complex. Carriers suitable for use to make up the feed supplement compositions include the following: soybean meal, alfalfa meal, cottonseed oil meal, linseed oil meal, cornmeal, cane molasses, urea, bone meal, corn cob meal, and the like. The carrier promotes a uniform distribution of the complex in the finished feed into which the supplement is blended. It thus performs an important function by ensuring proper distribution of the complex throughout the feed.

For a clearer understanding of the invention, specific examples of it are set forth below. These examples are merely illustrative, and are not to be understood as limiting the scope and underlying principles of the invention in any way.

EXAMPLE 1

Preparation of antibiotic trans-BM123$\gamma$ dioctyl sulfosuccinate complex from harvest mash filtrate To a 40 liter portion of Nocardia sp. NRRL 11,230 fermentation mash filtrate containing 533 mcg. of antibiotic trans-BM123$\gamma$ per ml., is added 800 g. of sodium chloride. The filtrate is adjusted to pH 4 with hydrochloric acid. A 600 g. portion of diatomaceous earth is added followed by one liter of an aqueous alcoholic solution of dioctyl sodium sulfosuccinate. The pH is readjusted to 4.0 with hydrochloric acid, 600 g. of diatomaceous earth is added and the mixture is stirred for 15 minutes. The mixture is allowed to settle for one hour and the supernatant is syphoned off. The pH of the settled material is adjusted to 5 with sodium hydroxide. The mixture is then freeze dried giving 3.02 kg. of material containing antibiotic trans-BM123$\gamma$ dioctyl sulfosuccinate complex.

EXAMPLE 2

Preparation of antibiotic trans-BM123$\gamma$ dioctyl sulfosuccinate complex from harvest mash filtrate To a 100 ml. portion of Nocardia sp. NRRL 11230 mash filtrate, assaying 582 mcg./ml. of antibiotic trans-BM123$\gamma$, is added with stirring 1.0 ml. of a 70% ethanolic solution of dioctyl sodium sulfosuccinate. The pH of the mixture is adjusted to 4.75 with 6 N hydrochloric acid and the mixture is centrifuged. The supernatant is decanted and the precipitate is dried in vacuo for 4 days without heat to give 1.54 g. of product.

EXAMPLE 3

Growth promoting effect of antibiotic trans-BM123$\gamma$ dioctyl sulfosuccinate complex on poultry One day old Hubbard X Hubbard crossbred chicks are used. These chicks are randomly allotted to pens of ten chicks (5 male and 5 female) each. Four experiments are started at one week intervals. In each experiment, four pens of chicks are used for unmedicated controls and two pens of chicks are used at each level of drug. Thus a total of 16 pens (160 chicks) are used as controls and a total of 8 pens (80 chicks) are used at each dose level of drug. The duration of the experiment is 14 days.

The controls are offered an unmedicated diet of broiler ration (composition follows) and water ad libitum. The medicated chicks are offered the same diet containing the antibiotic trans-BM123$\gamma$-dioctyl sulfosuccinate complex precipitated from fermentation mash filtrate, at levels of 5, 10, 20 and 40 parts per million, and water ad libitum. The weight of the chicks is determined at the beginning and on completion of the experiments. Weight gain and the amount of feed consumed are also determined. The data are averaged and summarized in Table I below, together with the percent improvement in weight gains and feed/gain ratios.

| Broiler ration formula: | |
|---|---|
| Component | Percent by weight |
| Ground yellow corn | 53.45 |
| Soybean oil meal (49%) | 28.00 |

| -continued | |
|---|---|
| Menhaden fish meal (60%) | 5.00 |
| Corn gluten meal (60%) | 5.00 |
| Dehydrated alfalfa meal (17%) | 2.00 |
| Stabilized fat | 4.00 |
| Dicalcium phosphate | 1.20 |
| Ground limestone | 0.50 |
| Sodium chloride | 0.30 |
| Trace minerals mixture* | 0.05 |
| Vitamin premix** | 0.50 |

*Trace mineral mixture

| Component | | One lb./ton furnishes |
|---|---|---|
| Manganese | 12.50% | 62.5 ppm |
| Iron | 6.00% | 30.0 ppm |
| Zinc | 5.00% | 25.0 ppm |
| Copper | 0.65% | 3.25 ppm |
| Iodine | 0.35% | 1.75 ppm |
| Cobalt | 0.25% | 1.25 ppm |
| Calcium (min. 15.30%, max. 18.35%) | | |

**Vitamin premix for one ton

| Component | Weight in grams |
|---|---|
| DL. Methionine | 453.6 |
| Butylated hydroxy toluene | 113.6 |
| Vitamin A (30,000 mcg./g.) | 100.0 |
| Vitamin $D_3$ (200,000 mcg./g.) | 5.0 |
| Vitamin E (20,000 mcg./g.) | 45.4 |
| Riboflavin | 4.0 |
| Niacinamide | 25.0 |
| Calcium pantothenate | 8.0 |
| Vitamin K (menadione) | 1.0 |
| Folic acid (10%) | 13.0 |
| Choline chloride (50%) | 908.0 |
| Vitamin $B_{12}$ (20 mg./lb.) | 227.0 |
| Corn oil | 50.0 |
| Fine ground corn | 2,582.4 |

TABLE I

| Treatment | Drug Level In Feed (ppm) | Av. Weight Per Chick In Grams | | Gain Per Chick In Grams | Feed Consumed Per Chick In Grams (Average) | Feed/Gain Ratio | % Improvement In | |
|---|---|---|---|---|---|---|---|---|
| | | Start | End | | | | Gain | Feed/Gain Ratio |
| Control | | 41.3 | 284.1 | 242.8 | 338.0 | 1.392 | | |
| Antibiotic trans- | 5 | 41.3 | 290.2 | 248.9 | 341.0 | 1.370 | 2.5 | 1.5 |
| BM123γ-Dioctyl | 10 | 41.3 | 302.3 | 261.0 | 346.9 | 1.329 | 7.5 | 4.5 |
| Sulfosuccinate | 20 | 41.3 | 297.1 | 255.8 | 343.0 | 1.341 | 5.3 | 3.7 |
| Complex Precipitated from Fermentation Mash Filtrate | 40 | 41.3 | 296.2 | 254.9 | 344.6 | 1.352 | 5.0 | 2.9 |

We claim:

1. A process of recovering an antibiotic trans-BM123γ-dioctyl sulfosuccinate complex from a fermentation whole harvest mash containing antibiotic trans-BM123γ which comprises the steps of:
   (a) producing a fermentation liquor by filtering the whole harvest mash;
   (b) acidifying the fermentation liquor to a pH of from 2.5 to 6.0 with a pharmacologically acceptable acid;
   (c) adding to the acidified liquor, in amount sufficient to produce a complex with the antibiotic trans-BM123γ, a complexing agent selected from the group consisting of the alkali metal and alkaline earth metal salts of sulfobutanedioic acid 1,4-bis(2-ethylhexyl)ester and mixtures thereof;
   (d) removing the precipitated antibiotic trans-BM123γ - dioctyl sulfosuccinate complex; and
   (e) drying the antibiotic trans-BM123γ-dioctyl sulfosuccinate complex.

2. A process as defined in claim 1 wherein the complexing agent is dioctyl sodium sulfosuccinate.

3. A process as defined in claim 1 wherein the complexing agent is dioctyl calcium sulfosuccinate.

4. A dry antibiotic trans-BM123γ-dioctyl sulfosuccinate complex prepared as defined in the process of claim 1.

5. An animal feed composition for improving feed efficiency and enhancing the growth rate of animals and poultry comprising a nutritionally balanced animal feed containing from about 0.0001% to about 1.0% by weight of the feed of an antibiotic trans-BM123γ-dioctyl sulfosuccinate complex prepared as defined in the process of claim 1.

6. A process for the production of a dried fermentation harvest mash solids animal feed supplement containing an antibiotic trans-BM123γ-dioctyl sulfosuccinate complex which comprises the steps of:
   (a) acidifying a fermentation whole harvest mash containing antibiotic trans-BM123γ to a pH from 2.5 to 6.0 with a pharmacologically acceptable acid;
   (b) adding to the acidified mash, in amount sufficient to produce a complex with the antibiotic trans-BM123γ, a complexing agent selected from the group consisting of the alkali metal and alkaline earth metal salts of sulfobutanedioic acid 1,4-bis(2-ethylhexyl)ester and mixtures thereof;
   (c) removing the harvest mash solids together with the precipitated antibiotic trans-BM123γ-dioctyl sulfosuccinate complex; and
   (d) drying the mixture of mash solids and antibiotic trans-BM123γ-dioctyl sulfosuccinate complex.

7. A process as defined in claim 6 wherein the complexing agent is dioctyl potassium sulfosuccinate.

8. A process as defined in claim 6 wherein the complexing agent is dioctyl magnesium sulfosuccinate.

9. An animal feed supplement of a dry mixture of fermentation harvest mash solids and an effective amount of antibiotic trans-BM123γ-dioctyl sulfosuccinate complex prepared as defined in the process of claim 6.

10. An animal feed composition for improving feed efficiency and enhancing the growth rate of animals and poultry comprising a nutritionally balanced animal feed containing from about 0.0001% to about 1.0% by weight of the feed of an animal feed supplement prepared as defined in the process of claim 6.

11. An animal feed premix for improving feed efficiency and enhancing the growth rate of animals and poultry comprising from about 70% to about 99% by weight of an edible carrier and from about 1% to about 30% by weight of an antibacterial ingredient selected from the group consisting of a dry complex as defined in claim 4, an animal feed supplement as defined in claim 9, and mixtures thereof in any proportion.

* * * * *